United States Patent [19]
Schmidt et al.

[11] 3,943,106
[45] Mar. 9, 1976

[54] POLYMERIC MALONATES

[75] Inventors: Andreas Schmidt, Reinach; Hansjörg Heller, Riehen, both of Switzerland

[73] Assignee: CIBA-GEIGY Corporation, Ardsley, N.Y.

[22] Filed: Apr. 30, 1973

[21] Appl. No.: 355,985

[30] Foreign Application Priority Data
May 4, 1972   Switzerland.......................... 6614/72

[52] U.S. Cl.................... 260/47 C; 260/6; 260/7.5; 260/22 R; 260/45.85 N; 260/45.9 NC; 260/47 CZ; 260/47 CP; 260/49; 260/473 R; 260/857 PE
[51] Int. Cl.²......................................... C08G 63/02
[58] Field of Search............. 260/47 R, 47 P, 45.85, 260/473 R, 473 S, 47 CP, 47 C, 47 CZ, 49

[56] References Cited
UNITED STATES PATENTS

| | | | |
|---|---|---|---|
| 3,464,990 | 9/1969 | Brossi et al. ...................... | 260/473 X |
| 3,494,887 | 2/1970 | Dexter et al. ..................... | 260/473 |

*Primary Examiner*—Harold D. Anderson
*Attorney, Agent, or Firm*—Nestor W. Shust

[57] ABSTRACT

The polymeric malonates of the invention have the formula

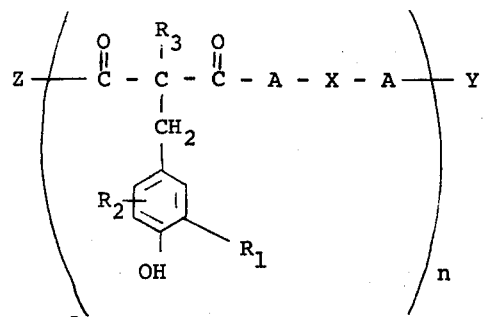

wherein
$R_1$ and $R_2$ are alkyl groups,
$R_3$ is an alkyl or hindered hydroxybenzyl group,
A is oxygen or amino group,
X is a divalent group such as unsubstituted or substituted alkylene or thioalkylene,
Y is hydrogen or a hindered hydroxybenzyl group,
Z is hydrogen, hydroxy, alkoxy or thioalkyl group, and $n$ is 2 to 100.

These compounds are prepared by reacting esters of malonates with divalent alcohols or with diamines and then with a monovalent alcohol. They are useful as stabilizers of organic materials subject to oxidative and thermal degradation.

3 Claims, No Drawings

POLYMERIC MALONATES

The present invention relates to new compounds, the methods for their manufacture, their use for stabilising organic material against thermo-oxidative degradation and the organic materials stabilised with their aid.

The new compounds correspond to the general formula

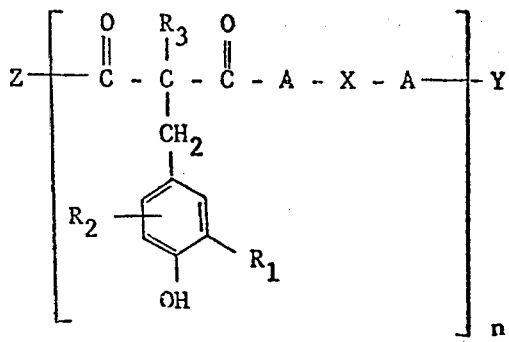

(I)

wherein $R_1$ denotes alkyl with 1 to 5 carbon atoms, cycloalkyl with 6 to 8 carbon atoms or aralkyl with 7 to 9 carbon atoms, $R_2$ denotes hydrogen, alkyl with 1 to 5 carbon atoms, cycloalkyl with 6 – 8 carbon atoms or aralkyl with 7 – 9 carbon atoms, $R_3$ denotes hydrogen, alkyl with 1 to 18 carbon atoms, or the group

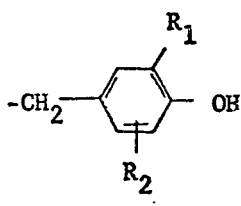

A denotes —O—; —NH—; or

wherein $R_4$ is an alkyl group with 1 – 4 carbon atoms, X denotes alkylene with 2 to 18 carbon atoms, alkenylene with 4 to 18 carbon atoms wherein A is linked to a saturated carbon atom in the alkenylene, oxaalkylene with 4 to 18 carbon atoms wherein A is linked to a carbon atom in the oxaalkylene which does not carry any further hetero-atoms, thiaalkylene with 4 to 18 carbon atoms wherein A is linked to a carbon atom in the thiaalkylene which does not carry any further hetero-atoms, mercaptoalkylene with 3 to 18 carbon atoms, alkylthioalkylene with 4 to 21 carbon atoms, hydroxyalkylene with 3 to 18 carbon atoms, acyloxyalkylene with 5 to 21 carbon atoms, phenoxyalkylene with 9 to 20 carbon atoms, or alkoxyalkylene with 4 to 21 carbon atoms, wherein the mercapto, alkylthio, hydroxyl, acyloxy, phenoxy or alkoxy group of the mercaptoalkylene, alkylthioalkylene, hydroxyalkylene, acyloxyalkylene, phenoxyalkylene or alkoxyalkylene is bonded to a carbon atom not linked to the group A, or a group

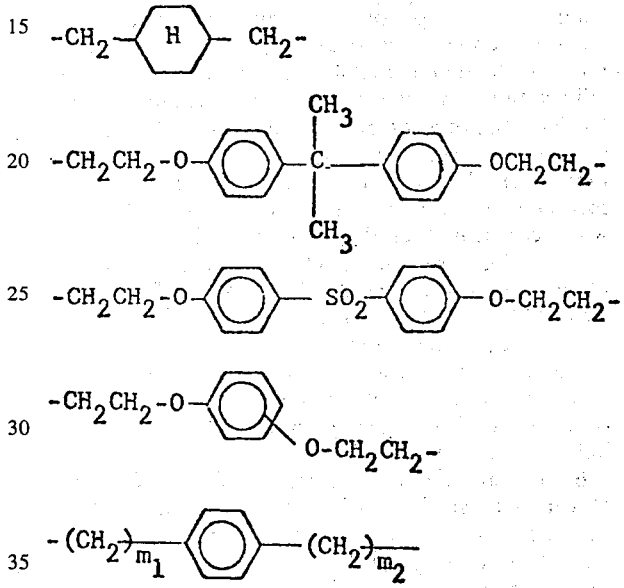

wherein $m_1$ and $m_2$ are 1, 2 or 3, Y denotes hydrogen or the group

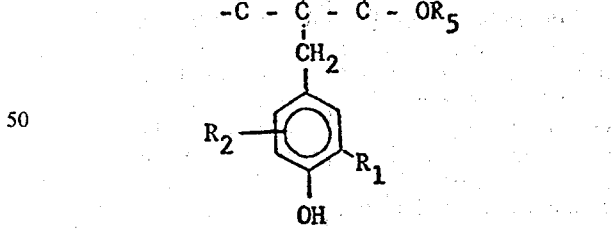

Z denotes $OR_5$ or, if Y denotes hydrogen, also denotes the group

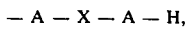

— A — X — A — H, with the abovementioned meanings for A and X and $R_5$ denotes hydrogen, alkyl with 1 to 18 carbon atoms, oxaalkyl with 3 to 20 carbon atoms, wherein the carbon atom in $R_5$ linked to oxygen does not carry any further hetero-atoms, thiaalkyl with 3 to 20 carbon atoms wherein the carbon atom in $R_5$ linked to the oxygen does not carry any further hetero-atoms, or 1-phospha-2,6,7-trioxabicyclo[2,2,2]-oct-4-yl-methyl, and $n$ denotes 2 to 100.

It has been found, surprisingly, that the compounds of the formula I are very suitable for stabilising organic material against thermo-oxidative degradation.

The new compounds show better activity than the previously known monomeric phenolic compounds of similar structure. This becomes particularly clear if polymeric material in the form of fibres and films is to be protected against autoxidation. Monomeric oxidation inhibitors are in part lost during the manufacture and shaping of the polymeric material, or under the use conditions, because of their volatility. On the other hand, the compounds according to the invention are non-volatile, non-extractable and of excellent compatibility with polymeric material, which manifests itself in the fact that efflorescence is not observed. The compounds are furthermore also soluble and effective in monomeric, liquid materials. The compounds according to the invention are either glassy supercooled melts which can be powdered, or viscous liquids of which the viscosity decreases very rapidly with increasing temperature, so that at temperatures around 100°C they can be handled effortlessly as liquids, which facilitates automatic continuous metering.

The compounds according to the invention can be manufactured in a simple manner in a one-pot process, so that expensive working up by crystallisation or distillation is avoided.

In the definition of the compounds of the formula I, $R_1$ can be alkyl with 1 - 5 carbon atoms and/or $R_2$ can be alkyl with 1 - 8 carbon atoms, such as, for example, methyl, ethyl, isopropyl, butyl, sec.-butyl, tert.-butyl, amyl, tert.-amyl, sec.-amyl, hexyl, octyl or tert.-octyl.

$R_1$ and/or $R_2$ can also be a cycloalkyl group with 6 - 8 carbon atoms, such as, for example, cyclohexyl, α-methylcyclohexyl or cyclooctyl, or an aralkyl group, such as benzyl or α-phenylethyl. $R_3$ and/or $R_5$ in the formula I can be alkyl with 1 - 18 carbon atoms, such as methyl, ethyl, propyl, butyl, pentyl, hexyl, octyl, decyl, dodecyl, tetradecyl or octadecyl.

$R_4$ in the formula I can be methyl, ethyl, propyl, isopropyl or butyl.

If the radical X in the definition of the formula I is alkylene, it can be, for example, ethylene, propylene, trimethylene, tetramethylene, hexamethylene, octamethylene, decamethylene or octadecamethylene. If X denotes alkenylene, it is, for example, butenylene, pentenylene, hexenylene, octenylene, decenylene, tetradecenylene or octadecenylene. X as oxaalkylene can be the divalent radical of 3-oxapentane, 3-oxaheptane, 3-oxaundecane, 3-oxapentadecane or 3-oxaheneicosane and X as thiaalkylene can denote the divalent radical of 3-thiapentane, 3-thiaheptane, 3-thiaundecane, 3-thiapentadecane, 3-thianonadecane, 3-thiaheneicosane or 4-thiadecane. When X denotes hydroxyalkylene it is, for example, 2-hydroxytrimethylene or 3-hydroxytetramethylene.

When X is acyloxyalkylene, acyl preferably denotes the radical of an aliphatic carboxylic acid such as of an alkanoic acid with 2 to 18 carbon atoms. Examples of such acids are acetic acid, propionic acid, caproic acid, lauric acid and stearic acid.

Examples of acyloxyalkylene are acetoxyalkylene, butyryloxyalkylene, lauroyloxyalkylene and stearoyloxyalkylene.

If X denotes alkoxyalkylene, it is, for example, methoxyalkylene, ethoxyalkylene, octoxyalkylene or octadecoxyalkylene.

If $R_5$ denotes oxaalkyl it can denote, for example, 3-oxabutyl, 2-oxapentyl, 2-oxaheptyl, 3-oxapentadecyl or 2-oxaheneicosyl, and if $R_5$ denotes thiaalkyl it can denote, for example, 3-thiabutyl, 3-thiapentyl, 3-thiaheptyl, 3-thiaundecyl, 3-thiapentadecyl, 3-thianonadecyl and 3-thiaheneicosyl.

Amongst the compounds of the formula I, those are preferred in which $R_1$ denotes methyl, isopropyl, sec.-butyl or tert.-butyl, $R_2$ denotes hydrogen or methyl, isopropyl, sec.-butyl, or tert.-butyl, $R_3$ denotes hydrogen or the group

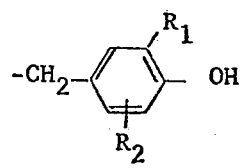

A denotes —O— or —NH—, X denotes alkylene with 2 to 18 carbon atoms or thiaalkylene with 4 to 18 carbon atoms, A being linked to a carbon atom in the thiaalkylene which does not carry any further hetero-atoms, Y denotes hydrogen or the group

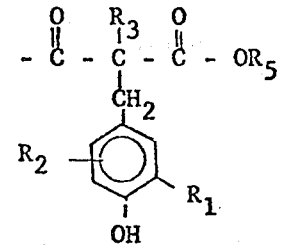

Z denotes $OR_5$ or, if Y denotes hydrogen, also denotes the group

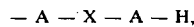

with the abovementioned meanings for A and X, $R_5$ denotes hydrogen, alkyl with 1 to 18 carbon atoms or thiaalkyl with 3 to 20 carbon atoms, wherein the carbon atom in $R_5$ bonded to oxygen does not carry any further hetero-atoms, and $n$ denotes 2 to 50.

Particularly preferred compounds of the formula I are those wherein $R_1$ denotes alkyl with 1 to 4 carbon atoms, $R_2$ denotes alkyl with 4 carbon atoms, $R_3$ denotes hydrogen, A denotes —O— or —NH—, X denotes alkylene with 5 to 9 carbon atoms, thiaalkylene with 4 carbon atoms, alkylthioalkylene with 21 carbon atoms, alkoxyalkylene with 21 carbon atoms, wherein A is linked to a carbon atom in the thiaalkylene, alkylthioalkylene or alkoxyalkylene which does not carry any further hetero-atoms, or the group —CH$_2$-CHOH—CH$_2$—, Y denotes hydrogen or the group

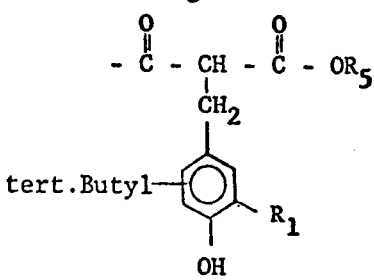

with $R_1$ being alkyl with 1 to 4 carbon atoms, and $R_5$ being alkyl with 1 to 18 carbon atoms, Z denotes alkoxy with 1 to 18 carbon atoms or 1-phospha-2,6,7-trioxabicyclo[2,2,2]oct-4-yl-methyl and $n$ denotes 2 – 20.

The manufacture of the compounds of the formula I can be effected, for example, by reaction of $m$ mols of a compound of the general formula II

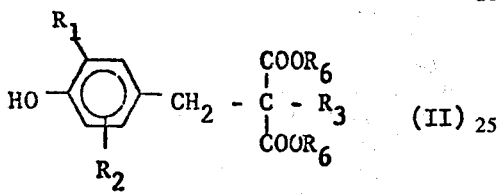

wherein $R_1$, $R_2$ and $R_3$ have the abovementioned meaning and $R_6$ denotes a lower alkyl group, preferably methyl or ethyl, with $n$ mols of a compound of the formula III $$HA - X - AH \qquad (III)$$

and $q$ mols of a compound of the formula IIIa $$R_5 - OH \qquad (IIIa)$$

wherein A and X have the abovementioned meaning and wherein $n$  $m$ and $q = 2$ ($m$ - $n$), in the presence of a basic catalyst. In the reaction, 2 $m$ mols of $R_6OH$ are split off.

A simplified manufacturing process consists of manufacturing the compounds of the formula II directly in the reaction mixture from a malonic acid ester of the formula IV

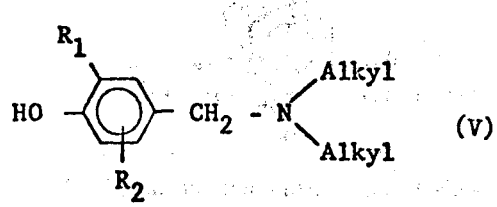

and a compound of the formula V

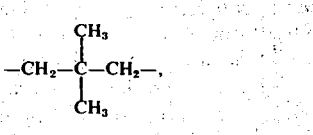

as described, for example, in Netherlands Pat. No. 68/03,498, in the presence of a basic catalyst and of the compounds of the formulae III and IIIa, which also leads to the compounds of the formula I.

Both the manufacturing processes described can be modified in that it is possible to employ two or more compounds of the formulae III and IIIa in the mixture.

In order to avoid a yellowish discolouration of the reaction mixture, a small amount of a phosphite can be added to the reaction mixture before adding the basic catalyst.

Examples of compounds of the formula I which show particularly good stabilising properties are the following:

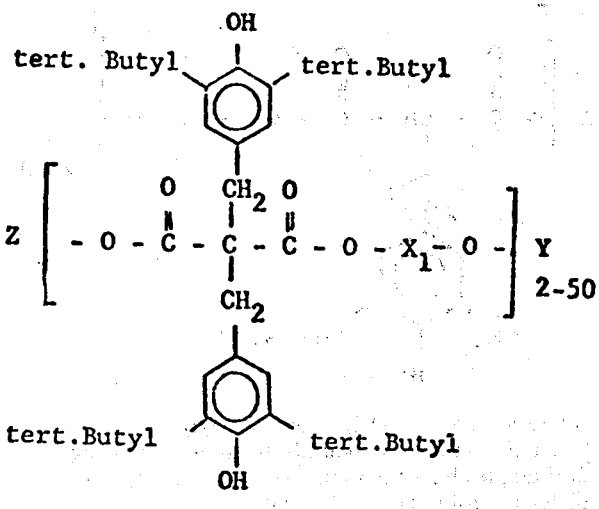

wherein $X_1$ denotes —$(CH_2)_6$—,

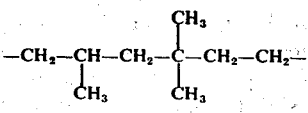

—$CH_2CH_2$—S—$CH_2CH_2$— or

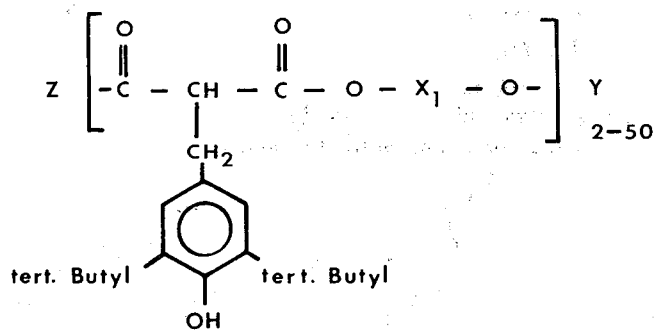

with the abovementioned meaning for $X_1$.

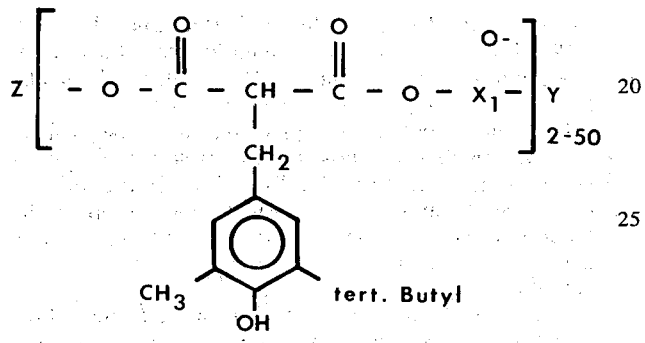

with the abovementioned meaning for $X_1$.

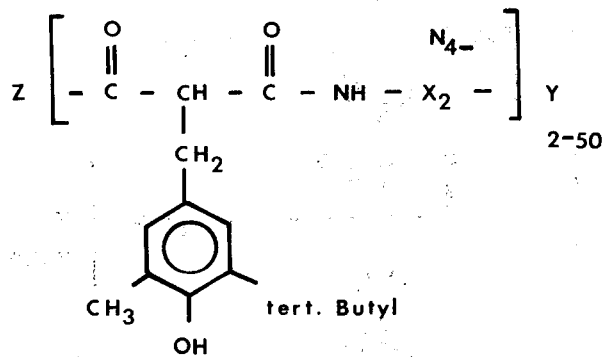

wherein $X_2$ is —(CH$_2$)$_6$— or —(CH$_2$)$_2$—.

Z and Y in the compounds mentioned above by way of examples have the same meaning as in the definition under the formula I.

The compounds of the formula I are used as stabilisers for organic substrates. As such it is possible to use, for example:

1. Polymers which are derived from hydrocarbons with single or double unsaturation, such as polyolefines, such as, for example, polyethylene, which can optionally be crosslinked, polypropylene, polyisobutylene, polymethylbutene-1, polymethylpentene-1, polybutene-1, polyisoprene, polybutadiene, polystyrene, polyisobutylene, copolymers of the monomers on which the homopolymers mentioned are based, such as ethylenepropylene copolymers, propylene-butene-1 copolymers, propylene-isobutylene copolymers, styrene-butadiene copolymers and terpolymers of ethylene and propylene with a diene, such as, for example, hexadiene, dicyclopentadiene or ethylidenenorbornene; mixtures of the abovementioned homopolymers, such as, for example, mixtures of polypropylene and polyethylene, polypropylene and polybutene-1, or polypropylene and polyisobutylene.
2. Vinyl polymers containing halogen, such as polyvinyl chloride, polyvinylidene chloride, polyvinyl fluoride, but also polychloroprene and chlorinated rubbers.
3. Polymers which are derived from α,β-unsaturated acids and their derivatives, such as polyacrylates and polymethacrylates, polyacrylamides and polyacrylonitrile, as well as their copolymers with other vinyl compounds, such as acrylonitrile/butadiene/styrene, acrylonitrile/styrene and acrylonitrile/styrene/acrylic ester copolymers.
4. Polymers which are derived from unsaturated alcohols and amines or their acyl derivatives or acetals, such as polyvinyl alcohol, polyvinyl acetate, polyvinyl stearate, polyvinyl benzoate, polyvinyl maleate, polyvinyl butyral, polyallyl phthalate, polyallyl melamine and their copolymers with other vinyl compounds, such as ethylene/vinyl acetate copolymers.
5. Homopolymers and copolymers which are derived from epoxides, such as polyethylene oxide or the polymers which are derived from bis-glycidyl ethers.
6. Polyacetals, such as polyoxymethylene and polyoxyethylene, as well as those polyoxymethylenes which contain ethylene oxide as the comonomer.
7. Polyphenylene oxides.
8. Polyurethanes and polyureas.
9. Polycarbonates.
10. Polysulphones.
11. Polyamides and copolyamides which are derived from diamines and dicarboxylic acids and/or from aminocarboxylic acids or the corresponding lactams, such as polyamide 6, polyamide 6/6, polyamide 6/10, polyamide 11 and polyamide 12.
12. Polyesters which are derived from dicarboxylic acids and dialcohols and/or from hydroxycarboxylic acids or the corresponding lactones, such as polyethylene glycol terephthalate or poly-1,4-dimethylolcyclohexane terephthalate.
13. Crosslinked polymers which are derived from aldehydes on the one hand and phenols, ureas and melamines on the other, such as phenol-formaldehyde, urea-formaldehyde and melamine-formaldehyde resins.
14. Alkyd resins, such as glycerine-phthalic acid resins and their mixtures with melamine-formaldehyde resins.
15. Unsaturated polyester resins which are derived from copolyesters of saturated and unsaturated dicarboxylic acids with polyhydric alcohols, with vinyl compounds as crosslinking agents, and also their halogen-containing modifications of low inflammability.
16. Natural polymers such as cellulose, rubber, proteins and their polymer-homologously chemically modified derivatives, such as cellulose acetates, cellulose propionates and cellulose butyrates, or the cellulose ethers, such as methylcellulose.
17. High molecular monomeric substances, for example mineral oils, animal and vegetable fats, oils and waxes, or oils, waxes and fats based on synthetic esters.

The compounds of the formula I are incorporated into the substrates in a concentration of 0.01 to 5% by weight calculated relative to the material to be stabilised.

Preferably, 0.05 to 2.0, and particularly preferentially 0.1 to 1.0, % by weight of the compounds, calculated relative to the material to be stabilised, are incorporated into the latter. The incorporation can take place before, during or after the polymerisation, for example by mixing in at least one of the compounds of the formula I and optionally further additives according to the methods customary in the art, before or during shaping, or by applying the dissolved or dispersed compounds to the polymer, if appropriate with subsequent evaporation of the solvent, In the case of crosslinked polyethylene, the compounds are added before crosslinking.

As further additives together with which the stabilisers can be employed, there should be mentioned;

1. Antioxidants of the aminoaryl and hydroxyaryl series. Amongst the latter, there should be mentioned the sterically hindered phenol compounds, for example:

A. Simple 2,6-dialkylphenols, such as, for example, 2,6-ditert.butyl-4-methylphenol, 2-tert.butyl-4,6-dimethylphenol, 2,6-ditert.butyl-4-methoxymethylphenol and 2,6-dioctadecyl-4-methylphenol.

B. Derivatives of alkylated hydroquinones, such as, for example, 2,5-ditert.butyl-hydroquinone, 2,5-ditert.amylhydroquinone, 2,6-ditert.butyl-hydroquinone, 2,5-ditert.butyl-4-hydroxy-anisole, 3,5-ditert.butyl-4-hydroxy-anisole and tris(3,5-ditert.butyl-4-hydroxyphenyl)-phosphite.

C. Hydroxylated thiodiphenyl ethers, such as, for example, 2,2'-thiobis-(6-tert.butyl-4-methylphenol), 2,2'-thiobis-(4-octylphenol), 4,4'-thiobis-(6-tert.butyl-3-methylphenol), 4,4'-thiobis-(3,6-di-sec.amylphenol) and 4,4'-thiobis-(6-tert.butyl-2-methylphenol).

D. Alkylidene-bisphenols, such as, for example, 2,2'-methylene-bis-(6-tert.butyl-4-methylphenol), 2,2-methylene-bis-(6-tert.butyl-4-ethylphenol), 4,4'-methylene-bis-(6-tert. butyl-2-methylphenol), 4,4'-methylene-bis-(2,6-ditert.butylphenol), 2,6-di(3-tert.butyl-5-methyl-2-hydroxybenzyl)-4-methylphenol, 2,2'-methylene-bis-[4-methyl-6-(α-methylcyclohexyl)-phenol], 1,1-bis-(3,5-dimethyl-2-hydroxyphenylbutane), 1,1-bis-(5-tert.butyl-4-hydroxy-2-methylphenyl)-butane, 2,2-bis-(5-tert.butyl-4-hydroxy-2-methylphenyl)-butane, 2,2-bis-(3,5-ditert.butyl-4-hydroxyphenyl)-propane, 1,1,3-tris-(5-tert.butyl-4-hydroxy-2-methylphenyl)-butane, 2,2-bis-(5-tert. butyl-4-hydroxy-2-methylphenyl)-4-n-dodecylmercapto-butane, 1,1,5,5-tetra-(5-tert.butyl-4-hydroxy-2-methylphenyl)-pentane and ethylene glycol bis-[3,3-bis-(3'-tert.butyl-4'-hydroxyphenyl)-butyrate].

E. O- N- and S-Benzyl compounds such as, for example, 3,5,3',5'-tetra-tert.butyl-4,4'-dihydroxydibenzyl ether, 4-hydroxy-3,5-dimethylbenzyl-mercaptoacetic acid octadecyl ester, tri-(3,5-ditert.butyl-4-hydroxybenzyl)-amine and the diester from terephthalic acid and 5-tert.butyl-4-hydroxy-2,3-dimethylbenzylmercaptan.

F. Hydroxybenzylated malonate esters, such as, for example, 2,2-bis-(3,5-di-tert.butyl-2-hydroxybenzyl)-malonic acid dioctadecyl ester, 2-(3-tert.butyl-4-hydroxy-5-methylbenzyl)-malonic acid dioctadecyl ester, 2,2-bis-(3,5-di-tert. butyl-4-hydroxybenzyl)-malonic acid didodecylmercapto ethyl ester and 2,2-bis-(3,5-di-tert.butyl-4-hydroxybenzyl)-malonic acid di-(4-tert.octylphenyl)-ester.

G. Hydroxybenzyl-aromatics, such as, for example, 1,3,5-tri-(3,5-di-tert.butyl-4-hydroxybenzyl)-2,4,6-trimethylbenzene, 1,4-di-(3,5-di-tert.butyl-4-hydroxybenzyl)-2,3,5,6-tetramethylbenzene, and 2,4,6-tri-(3,5-di-tert.butyl-4-hydroxybenzyl)-phenol.

H. s-Triazine compounds, such as, for example, 2,4-bis-octylmercapto-6-(3,5-di-tert.butyl-4-hydroxy-anilino)-s-triazine, 2-octylmercapto-4,6-bis-(3,5-di-tert.butyl-4-hydroxyanilino)-s-triazine, 2-octylmercapto-4,6-bis-(3,5-di-tert.butyl-4-hydroxy-phenoxy)-s-triazine, 2,4,6-tris-(3,5-di-tert.butyl-4-hydroxyphenoxy)-s-triazine, 2,4,6-tris-(3,5-di-tert.butyl-4-hydroxyphenylethyl)-s-triazine and 1,3,5-tris-(3,5-di-tert. butyl-4-hydroxybenzyl)-isocyanurate.

I. Amides of 3,5,di-tert.butyl-4-hydroxyphenylpropionic acid, such as, for example, 1,3,3-tri-(3,5-di-tert. butyl-4-hydroxyphenyl-propionyl)-hexahydro-s-triazine and N,N'-di-(3,5-di-tert.butyl-4-hydroxyphenyl-propionyl)-hexamethylenediamine.

K. Esters of 3,5-di-tert.butyl-4-hydroxyphenyl-propionic acid with monohydric or polyhydric alcohols, such as, for example, methanol, ethanol and octadecanol; 1,6-hexanediol; 1,9-nonandediol and ethylene glycol; 1,2-propanediol, diethylene glycol, thiodiethylene glycol, neopentyl glycol, 3-thia-undecanol, 3-thiapentadecanol, trimethylhexanediol, trimethylolethane, trimethylolpropane, tris-hydroxyethylisocyanurate and 4-hydroxymethyl-1-phospha-2,6,7-trioxabicyclo-[2,2,2]octane.

L. Esters of 5-tert.butyl-4-hydroxy-3-methylphenylpropionic acid with monohydric or polydydric alcohols, such as for example, methanol, ethanol and octadecanol; 1,6-hexanediol; 1,9-nonanediol and ethylene glycol;' 1,2-propanediol, diethylene glycol, thiodiethylene glycol, neopentyl glycol, 3-thia-undecanol, 3-thia-pentadecanol, trimethylhexanediol, trimethylolethane, trimethylolpropane, tris-hydroxyethylisocyanurate and 4-hydroxymethyl-1-phospha-2,6,7-trioxabicyclo[2,2,2]octane.

M. Esters of 3,5-di-tert.butyl-4-hydroxyphenylacetic acid with monohydric or polyhydric alcohols, such as, for example, methanol, ethanol and octadecanol; 1,6-hexanediol; 1,9-nonanediol, ethylene glycol, 1,2-propanediol, diethyleneglycol, thiodiethylene glycol, neopentyl glycol, 3-thia-undecanol, 3-thia-pentadecanol, trimethylhexanediol, trimethylolethane, trimethylolpropane, tris-hydroxyethyl-isocyanurate, and 4-hydroxymethyl-1-phospha-2,6,7-trioxabicyclo[2,2,2]octane.

N. Acylaminophenols, such as, for example, N-(3,5-ditert.butyl-4-hydroxyphenyl)-stearic acid amide and N,N'-di-(3,5-di-tert.butyl-4-hydroxyphenyl)-thiobisacetamide.

O. Benzylphosphates, such as, for example, 3,5-di-tert. butyl-4-hydroxybenzyl-phosphonic acid dimethyl ester, 3,5-ditert.butyl-4-hydroxybenzyl-phosphonic acid diethyl ester, 3,5-di-tert.butyl-4-hydroxybenzyl-phosphonic acid dioctadecyl ester and 5-tert.butyl-4-hydroxy-3-methylbenzyl-phosphonic acid dioctadecyl ester.

Amongst the aminoaryl derivatives there should be mentioned aniline and naphthylamine derivatives as well as their heterocyclic derivatives, for example: Phenyl-1-naphthylamine, phenyl-2-naphthylamine, N,N'-diphenyl-p-phenylenediamine, N,N'-di-2-naphthyl-p-phenylenediamine, N,N'-disec.butyl-p-phenylenediamine, 6-ethoxy-2,2,4-trimethyl-1,2-dihydroquinoline, 6-dodecyl-2,2,4-trimethyl-1,2-dihydroquinoline, monooctyliminodibenzyl and dioctyliminodibenzyl and polymerised 2,2,4-trimethyl-1,2-dihydroquinoline, though in the case of the combined use of the compounds of the formula I with the abovementioned amine compounds the stabilised polymer no longer has such good colour properties, because of the tendency of the amine compounds to discolour.

2. UV absorbers and light protection agents such as:
a. 2-(2'-hydroxyphenyl)-benztriazoles, for example the 5'-methyl-, 3',5'-di-tert.butyl-, 5'-tert.butyl-, 5-chloro-3'-, 5'-tert.butyl-, 5-chloro-3'-tert.butyl-5'-methyl-, 3'-sec. butyl-5'-tert.butyl-, 3'-[α-methylbenzyl]-5'-methyl-, 3'[α-methylbenzyl]-5'-methyl-5-chloro-, 4'-octoxy-, 3',5'-di-tert. amyl-, 3'-methyl-5'-carbomethoxyethyl- and 5-chloro-3',5'-ditert.amyl-derivative.
b. 2,4-Bis-(2'-hydroxyphenyl)-6-alkyl-s-triazines, for example the 6-ethyl- or 6-undecyl-derivative.
c. 2-Hydroxy-benzophenones, for example the 4-hydroxy-, 4-methoxy-, 4-octoxy-, 4-decyloxy-, 4-dodecyloxy-, 4,2',4'-trihydroxy- or 2'-hydroxy-4,4'-dimethoxy-derivative.
d. 1,3-Bis-(2'-hydroxy-benzoyl)-benzenes, for example 1,3-bis-(2'-hydroxy-4'-hexyloxy-benzoyl)-benzene, 1,3-bis-(2'-hydroxy-4'-octoxy-benzoyl)-benzene, and 1,3-bis-(2'-hydroxy-4'-dodecyloxy-benzoyl)-benzene.
e. Aryl esters of optionally substituted benzoic acids such as, for example, phenyl salicylate, octylphenyl salicylate, di-benzoylresorcinol, bis-(4-tert.butylbenzoyl)-resorcinol, benzoylresorcinol and 3,5-di-tert.-butyl-4-hydroxybenzoic acid 2,4-di-tert.butyl-phenyl ester, octadecyl ester or 2-methyl4,6-di-tert.butyl-phenyl ester.
f. Acrylates, for example α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester and N-(β-carbomethoxy-vinyl)-2-methyl-indoline.
g. Nickel compounds, for example nickel complexes of 2,2'-thiobis-(4-tert.octylphenol), such as the 1:1 and 1:2 complex, optionally with other ligands such as n-butylamine, nickel complexes of bis-(4-tert.octylphenyl)-sulphone, such as the 2:1 complex, optionally with other ligands such as 2-ethylcaproic acid, nickel dibutyldithiocarbamate, nickel salts of 4-hydroxy-3,5-di-tert.butylbenzyl-phosphonic acid monoalkyl esters such as the methyl, ethyl or butyl ester, the nickel complex of 2-hydroxy-4-methyl-phenyl-undecylketoxime and nickel 3,5-di-tert.butyl-4-hydroxy-benzoate.
h. Oxalic acid diamines, for example 4,4'-di-octyloxy oxanilide, 2,2'-di-octyloxy-5,5'-di-tert.butyl-oxanilide and 2,2'-di-dodecyloxy-5,5'-di-tert.butyl-oxanilide.

3. Phosphites, such as triphenylphosphite, diphenylalkylphosphites, phenyldialkylphosphites, trinonylphenylphosphite, trilaurylphosphite, trioctadecylphosphite, 3,9-di-isodecyloxy-2,4,8,10-tetraoxa-3,9-diphosphaspiro-(5,5)-undecane and tri-(4-hydroxy-3,5-di-tert.butylphenyl)-phosphite.

4. Compounds which destroy peroxides, such as esters of β-thiodipropionic acid, for example the lauryl, stearyl, myristyl or tridecyl esters, salts of 2-mercaptobenzimidazole, for example the zinc salt, and diphenylthiourea for polyolefines.

5. Polyamide stabilisers, such as copper salts in combination with iodides and/or further phosphorus compounds and salts of divalent manganese.

6. Basic co-stabilisers, such as polyvinyl pyrrolidone, melamine, benzoguanamine, triallyl-cyanurate, dicyandiamide, urea derivatives, hydrazine derivatives, amines, polyamides, polyurethanes, and alkali metal salts and alkaline earth metal salts of higher saturated or unsaturated fatty acids such as, for example, Ca stearate.

7. PVC stabilisers such as organic tin compounds, organic lead compounds and Ba/Cd salts of fatty acids.

8. Nucleating agents, such as 4-tert.butylbenzoic acid, adipic acid and diphenylacetic acid.

9. Other additives such as plasticisers, lubricants for example glycerine monostearate, emulsifiers, antistatic agents, flameproofing agents, pigments, carbon black, asbestos, glass fibres, kaolin and talc.

The invention is explained in more detail in the examples which follow.

EXAMPLE 1

56.9 g (0.1 mol) of bis(3,5-di-tert.butyl-4-hydroxybenzyl)-malonic acid dimethyl ester and 11.8 g (0.1 mol) of 1,6-hexanediol are heated to 150°C under nitrogen. Addition of 0.1 g (0.00435 mol) of lithium amide starts the reaction, which manifests itself by a vigorous evolution of methanol after application of a vacuum of 15 mm Hg. The elimination of methanol subsides after approx. 10 minutes. After cooling, the vacuum is released with nitrogen and the mixture is neutralised with glacial acetic acid, the entire melt is taken up in toluene, insoluble matter is filtered off and the filtrate is concentrated to dryness in vacuo. A yellow-brownish resin is thus obtained, which is solid at room temperature (Stabiliser No. 1).

If in this example the 1,6-hexanediol is replaced by an equimolecular amount of 2,4,4-trimethylhexanediol but otherwise the same procedure is followed, a highly viscous liquid is obtained (Stabiliser No. 2). If the 1,6-hexanediol is replaced by an equimolar amount of thiodiethylene glycol, a resin which can be powdered is obtained (Stabiliser No. 3).

EXAMPLE 2

44 g (0.125 mol) of (3,5-di-tert.butyl-4-hydroxybenzyl)malonic acid dimethyl ester and 13 g (0.125 mol) of 2,2-dimethyl-propanediol-(1,3) are warmed to 80°C under nitrogen. After adding 0.2 g (0.0087 mol) of $LiNH_2$ this temperature is maintained for 30 minutes at 15 mm Hg pressure. The initially vigorous elimination of methanol subsides during this time. After cooling, releasing the vacuum with nitrogen and neutralising with glacial acetic acid, the melt is taken up in toluene, insoluble matter is filtered off and the filtrate is evaporated to dryness in vacuo. An almost colourless resin is thus obtained, which is solid at room temperature and can readily be powdered (Stabiliser No. 4).

If, in this example, 2,2-dimethylpropanediol is replaced by the equimolecular amount of a polyol of Table 1 given below and otherwise the same procedure is followed, the polymeric compounds in which the diol unit is correspondingly replaced, are obtained.

Table 1

| Diol | Stabiliser No. | Physical state |
| --- | --- | --- |
| HO—(CH$_2$)$_6$—OH | 5 | Highly viscous liquid |
| HOCH$_2$—CH(OH)—CH$_2$OH | 6 | Resin which can be powdered |
| HO(CH$_2$)$_2$S(CH$_2$)$_2$OH | 7 | Highly viscous liquid |

EXAMPLE 3

29.8 g (0.05 mol) of bis-(3,5-di-tert.butyl-4-hydroxybenzyl)-malonic benzyl)-malonic acid diethyl ester, 5.90 g (0.05 mol) of 1,6-hexanediol, and 1.24 g (0.01 mol) of trimethylphosphite are heated to 135°C under nitrogen. 0.27 g (0.005 mol) of sodium methylate are now added to the clear melt and the mixture is left to react for 25 minutes under a vacuum of 15 mm Hg whilst stirring vigorously. The initially vigorous elimination of methanol subsides during this time. After cooling, releasing the vacuum with nitrogen and neutralising with glacial acetic acid, the entire melt is taken up in toluene, the insoluble matter is filtered off and the filtrate is concentrated to dryness in vacuo. An almost colourless resin (Stabiliser No. 8) is thus obtained, which can be powdered at room temperature.

EXAMPLE 4

6.6 g (0.05 mol) of malonic acid dimethyl ester, 13.18 g (0.05 mol) of N,N-dimethyl-(3,5-di-tert.butyl-4-hydroxy)-benzylamine, 4.73 g (0.04 mol) of 1,6-hexanediol and 1.64 g (0.01 mol) of 4-hydroxymethyl-1-phospha-2,6,7-trioxabicyclo [2,2,2]-octane are heated to 90°C under nitrogen. 0.27 g (0.005 mol) of sodium methylate is now added to the clear melt and the mixture is maintained for 1 hour at 85° – 95°C under a vacuum of 15 mm Hg, whilst stirring vigorously. The initially vigorous elimination of methanol and dimethylamine subsides during this time. After cooling, releasing the vacuum with nitrogen and neutralising with glacial acetic acid, the entire melt is taken up in toluene, insoluble matter is filtered off and the filtrate is concentrated to dryness in vacuo. An almost colourless (slightly yellowish) resin (Stabiliser No. 9) is thus obtained, which can be powdered at room temperature.

EXAMPLE 5

6.6 g (0.05 mol) of malonic acid dimethyl ester, 11.05 g (0.05 mol) of N,N-dimethyl-(3-methyl-5-tert.butyl-4-hydroxy)-benzylamine, 5.9 g (0.05 mol) of 1,6-hexanediol and 1 g of trisnonylphenylphosphite are heated to 90°C under nitrogen. 0.27 g (0.005 mol) of sodium methylate is now added to the clear melt and the mixture is maintained for 1 hour at 85° – 95°C under a vacuum of 15 mm Hg, whilst stirring vigorously. The initially vigorous elimination of methanol and dimethylamine subsides during this time. After cooling, releasing the vacuum with nitrogen and neutralising with glacial acetic acid, the entire melt is taken up in toluene, insoluble matter is filtered off and the filtrate is concentrated to dryness in vacuo. An almost colourless resin (Stabiliser No. 10) is thus obtained, which can be powdered at room temperature. The product has an average molecular weight of 11,800 as found by light scattering measurements.

If in this example the 1,6-hexanediol is replaced by the equivalent amount of 4-thiadocosane-1,2-diol or 4-oxa-docosane-1,2-diol, and otherwise identical conditions are used, the corresponding polymeric malonates are obtained (Stabiliser No. 14 and Stabiliser No. 15, respectively).

EXAMPLE 6

15.4 g (0.05 mol) of (3-methyl-5-tert.butyl-4-hydroxybenzyl)-malonic acid dimethyl ester, 5.8 g (0.05 mol) of hexamethylenediamine and 0.4 g of trisnonylphenylphosphite are heated to 120°C under nitrogen and stirred vigorously for 2 hours at this temperature. The methanol eliminated is condensed in a cold trap. Thereafter the mixture is kept additionally for 30 minutes under reduced pressure (15 mm Hg) at 125°C. After cooling, and releasing the vacuum with nitrogen, a light-coloured resin which is solid at room temperature is obtained (Stabiliser No. 11).

EXAMPLE 7

15 g (0.114 mol) of malonic acid dimethyl ester, 25 g (0.114 mol) of N,N-dimethyl-(3-methyl-5-tert.butyl-4-hydroxy)-benzylamine, 11.8 g (0.101 mol) of hexamethylenediamine and 1.5 g of trisnonylphenylphosphite are heated to 70°C under nitrogen. 0.1 g (approx. 0.005 mol) of lithium amide is added to the melt and the mixture is kept at 100°C for 1 hour whilst stirring vigorously and passing nitrogen through it. Thereafter the apparatus is evacuated to 15 mm Hg and the mixture is stirred for a further hour at 100°C. After cooling, releasing the vacuum with nitrogen and neutralising with glacial acetic acid, the entire melt is taken up in toluene, insoluble matter is filtered off and the filtrate is concentrated to dryness in vacuo. A light-coloured resin which is solid at room temperature is thus obtained (Stabiliser No. 12).

EXAMPLE 8

13.2 g (0.1 mol) of malonic acid dimethyl ester, 22.1 g (0.1 mol) of N,N-dimethyl-(3-methyl-5-tert.butyl-4-hydroxy)-benzylamine, 5.9 g (0.05 mol) of 1,6-hexanediol, 27 g (0.1 mol) of octadecanol and 2 g of trisnonylphenylphosphite are heated to 70°C under nitrogen. 0.5 g (approx. 0.02 mol) of lithium amide is added to the clear melt and the mixture is first held for 30 minutes at this temperature under a vacuum of 15 mm Hg, whilst stirring vigorously, and is then heated to 100°C over the course of a further 30 minutes. The initially vigorous elimination of methanol and dimethylamine subsides after this time. After cooling, releasing the vacuum with nitrogen and neutralising with glacial acetic acid, the entire melt is taken up in toluene, insoluble matter is filtered off and the filtrate is concentrated to dryness in vacuo. An almost colourless viscous liquid is thus obtained, which is infinitely miscible with hexane at room temperature. (Stabiliser No. 13).

If, in this example, the 1,6-hexanediol is replaced by the equivalent amount of thiodiethylene glycol, and otherwise identical conditions are used, a colourless substance of waxy consistency is obtained. (Stabiliser No. 16).

EXAMPLE 9

51.2 g (0.1 mol) of bis(3,5-diisopropyl-4-hydroxybenzyl)-malonic acid dimethyl ester, 10.4 g (0.06 mol) of 1,10-decanediol and 10.4 g (0.08 mol) of n-octanol are heated to 110°C under nitrogen. After adding 0.1 g (0.0043 mol) of lithium amide, a vacuum is applied and the temperature is maintained until the evolution of methanol has ceased, which is the case after approx. 30 minutes. After cooling, the vacuum is released with nitrogen, the mixture is neutralised with glacial acetic acid and the reaction product is boiled up in toluene. After filtration and evaporation, a highly viscous liquid which is infinitely soluble in aliphatic hydrocarbons is obtained.

EXAMPLE 10

40.6 g (0.1 mol) of 2-n-butyl-2-(3,5-ditert.-butyl-4-hydroxybenzyl)-malonic acid dimethyl ester, 25.7 g (0.09 mol) of 1,18-octadecanediol and 1.5 g (0.02 mol) of n-butanol are heated to 80°C under nitrogen. 0.3 g (0.0055 mol) of sodium methylate is added to the clear melt, whereupon methanol slowly distils off. After approx. 3 hours the mixture is cooled and neutralised with a little glacial acetic acid, and the reaction product is directly dissolved in petroleum ether. A slightly yellowish clear stabiliser solution is obtained.

If, in this example, the 2-n-butyl-2-(3,5-di-tert.-butyl-4-hydroxybenzyl)-malonic acid dimethyl ester is replaced by an equivalent amount of 2-n-octadecyl-2-(3,5-di-tert.-butyl-4-hydroxybenzyl)-malonic acid dimethyl ester and otherwise identical reaction conditions are used, a slightly yellowish resin is obtained which is infinitely soluble in benzene.

EXAMPLE 11

13.2 g (0.1 mol) of malonic acid dimethyl ester, 29.0 g (0.1 mol) of N,N-dimethyl-(3,5-ditert.-amyl-4-hydroxy)-benzylamine, 4.4 g (0.05 mol) of 1,4-butenediol, 19.0 g (0.1 mol) of 3-thia-undecanol and 2 g of tris-nonylphenylphosphite are heated to 70°C under nitrogen. 0.5 g (0.02 mol) of lithium amide is added to the clear melt and the mixture is kept, under a vacuum of 15 mm Hg and whilst stirring, for 1 hour at 70°C and then for a further hour at 110°C. During the reaction, the theoretical amounts of methanol and dimethylamine are eliminated. After cooling, releasing the vacuum with nitrogen and neutralising with glacial acetic acid, the mixture is dissolved in toluene and the solution is filtered and evaporated. A light-coloured resin which is highly viscous at room temperature is thus obtained.

EXAMPLE 12

56.9 g (0.1 mol) of bis-(3,5-ditert.-butyl-4-hydroxybenzyl)-malonic acid dimethyl ester, 10.5 g (0.07 mol) of 4-thia-1,7-heptanediol, 5.4 g (0.06 mol) of 3-oxa-pentanol-(1) and 2 g of tris-nonylphenyl-phosphite are heated to 130°C under nitrogen. The addition of 0.43 g (0.01 mol) of calcium hydride causes a vigorous elimination of methanol. The reaction vessel is evacuated to 15 mm Hg and the temperature is left at 130°C for 1 hour. After cooling, the vacuum is released with nitrogen, the mixture is neutralised with a little acetic acid and the reaction product is dissolved in hot ligroin. The insoluble constituents are filtered off. The resulting solution can be used directly as a stabiliser or can be evaporated, which yields the stabiliser as a honey-like liquid.

If, in this example, 3-oxa-pentanol-(1) is replaced by an equivalent amount of one of the alcohols of the list given below, reaction products which are similar to one another are obtained but which can show individual differences with regard to flow behaviour and solubility: 3-oxa-undecanol-(1); 3-oxa-pentadecanol-(1); 4-oxa-hexadecanol-(1); 3-thia-pentanol-(1); 3-thia-undecanol-(1); 3-thia-pentadecanol-(1); 4-thia-hexadecanol-(1); 4-hydroxymethyl-1-phospha-2,6,7-trioxabicyclo[2,2,2]-octane.

EXAMPLE 13

56.9 g (0.1 mol) of bis-(3,5-ditert.-butyl-4-hydroxybenzyl)-malonic acid dimethyl ester, 14.4 g (0.1 mol) of N,N-dimethylhexamethylenediamine and 1.5 g of tris-nonylphenylphosphite are heated to 120°C under nitrogen. 0.1 g of lithium amide is added to the clear melt and the temperature is then kept at 120°C for 1 hour whilst stirring vigorously. Thereafter the apparatus is evacuated to 15 mm Hg and the mixture is stirred for a further hour at 120°C. After cooling, releasing the vacuum with nitrogen and neutralising with glacial acetic acid, the melt is boiled up in toluene, insoluble matter is filtered off and the filtrate is evaporated to dryness in vacuo. A slightly yellow resin which is solid at room temperature and can be powdered is thus obtained.

EXAMPLE 14

75.6 g (0.1 mol) of bis(3,5-di(1-methylcyclohexyl)-4-hydroxybenzyl)-malonic acid diethyl ester and 11.8 g (0.1 mol) of 1,6-hexanediol are heated to 150°C under nitrogen. Addition of 0.1 g of lithium amide starts the reaction, and this manifests itself by a vigorous evolution of methanol after application of a vacuum of 15 mm Hg. The evolution of methanol subsides after approx. 10 minutes. After cooling, the pressure is released with nitrogen and the mixture is neutralised with glacial acetic acid, the entire melt is taken up in toluene, insoluble matter is filtered off and the filtrate is evaporated to dryness in vacuo. A yellow resin is thus obtained, which is a hard glass at room temperature.

EXAMPLE 15

59.6 g (0.1 mol) of bis-(3,5-ditert.-butyl-4-hydroxybenzyl)-malonic acid diethyl ester and 32.6 g (0.1 mol) of 2,2-bis-(4-hydroxyethoxyphenyl)-propane are heated to 150°C under nitrogen. Addition of 0.1 g of lithium amide starts the reaction, which manifests itself by a vigorous evolution of methanol after application of a vacuum of 15 mm Hg. The evolution of methanol subsides after approx. 10 minutes. After cooling, the pressure is released with nitrogen and the mixture is neutralised with glacial acetic acid, the entire melt is taken up in toluene, insoluble matter is filtered off and the filtrate is evaporated to dryness in vacuo. A yellow resin is thus obtained, which is a hard glass at room temperature.

If, in this example, 2,2-bis-(4-hydroxyethoxyphenyl)-propane is replaced by an equivalent amount of one of the diols of the list given below, reaction products which are similar to one another are obtained but which can show individual differences in appearance: 1,4-bis-hydroxymethyl-cyclohexane; bis-4-hydroxyethoxyphenyl-sulphone; m-dihydroxyethoxy-benzene; p-dihydroxyethoxybenzene; p-dihydroxymethylbenzene; p-dihydroxyethylbenzene and p-dihydroxypropylbenzene.

EXAMPLE 16

100 parts of polypropylene (melt index 3.2 g/10 minutes, 230°C/2,160 g) are thoroughly mixed for 10 minutes in a shaking apparatus, with 0.2 part of one of the additives listed in Table 2 below.

The resulting mixtures are kneaded for 10 minutes in a Brabender plastograph at 200°C and the mass thus obtained is subsequently pressed in a sheet press at 260°C platen temperature to give 1 mm thick sheets from which strips 1 cm wide and 17 cm long are punched.

The activity of the additives added to the test strips is tested by heat aging in a circulating air oven at 135°C and 149°C, an additive-free test strip serving for comparison. 3 test strips of each formulation are employed. The end point is defined as the incipient, easily visible decomposition of the test strip. The results are quoted in days.

Table 2

| Stabiliser No. | Days to incipient decomposition | |
|---|---|---|
| | 149°C | 135°C |
| without additive | ½ | 1 |
| 1 | 34 | 130 |
| 2 | 25 | 132 |
| 3 | 27 | 98 |
| 4 | 30 | 116 |
| 5 | 39 | 148 |
| 6 | 35 | 126 |
| 7 | 30 | 107 |
| 8 | 27 | 77 |
| 9 | 29 | 77 |
| 10 | 33 | 102 |
| 11 | 29 | 120 |
| 12 | 28 | 110 |
| 13 | 36 | 131 |
| 14 | 40 | 145 |
| 15 | 31 | 98 |
| 16 | 37 | 130 |

EXAMPLE 17

100 parts of polypropylene (melt index 3.2 g/10 minutes, 230°C/2,160 g) are thoroughly mixed for 10 minutes in a shaking apparatus, with 0.1 part of one of the additives listed in Table 3 below and 0.3 part of thiodipropionic acid dilauryl ester.

The resulting mixtures are kneaded for 10 minutes in a Brabender plastograph at 200°C and the mass thus obtained is subsequently pressed in a sheet press at 260°C platen temperature to give 1 mm thick sheets from which strips 1 cm wide and 17 cm long are punched.

The activity of the additives added to the test strips is tested by heat aging in a circulating air oven at 135°C and 149°C, using for comparison a test strip which only contains 0.3 part of thiodipropionic acid dilauryl ester.

For this purpose, 3 test strips of each formulation are employed. The end point is defined as the incipient, easily visible decomposition of the test strip. The results are quoted in days.

Table 3

| Stabiliser No. | Days to incipient decomposition | |
|---|---|---|
| | 149°C | 135°C |
| without additive | 8 | 20 |
| 1 | 49 | 163 |
| 2 | 48 | 157 |
| 3 | 26 | 112 |
| 4 | 35 | 130 |
| 5 | 38 | 141 |
| 6 | 37 | 129 |
| 7 | 35 | 126 |
| 8 | 25 | 119 |
| 9 | 28 | 121 |
| 10 | 43 | 132 |
| 11 | 31 | 130 |
| 12 | 35 | 139 |
| 13 | 42 | 151 |
| 14 | 42 | 135 |
| 15 | 35 | 110 |
| 16 | 33 | 122 |

EXAMPLE 18

Filings (chips) 25 μ thick are cut with the aid of a microtome from the 1 mm thick test sheets described in Example 16. These chips are clamped between grids of stainless steel and the sample carriers thus obtained are suspended in a circulating air oven and aged at 135°C or 147°C. The end point is defined as the time after which, on gently tapping the grid, degraded polypropylene drops out in the form of a powder (checked 1 – 2 x daily). The results are quoted in hours.

Table 4

| Stabiliser No. | Hours to incipient decomposition | |
|---|---|---|
| | 147°C | 135°C |
| without additive | 10 | 20 |
| 1 | 165 | 670 |
| 2 | 135 | 550 |
| 3 | 120 | 410 |
| 4 | 90 | 450 |
| 5 | 120 | 450 |
| 6 | 165 | 580 |
| 7 | 120 | 420 |
| 8 | 170 | 590 |
| 9 | 170 | 570 |
| 10 | 95 | 430 |
| 11 | 120 | 510 |
| 12 | 100 | 500 |
| 13 | 160 | 570 |
| 14 | 165 | 600 |
| 15 | 120 | 550 |
| 16 | 150 | 590 |

EXAMPLE 19

Filings (chips) 25 μ thick are cut with the aid of a microtome from the 1 mm thick test sheets described in Example 17. These chips are clamped between grids of stainless steel and the sample carriers thus obtained are suspended in a circulating air oven and aged at 135°C or 147°C. The end point is defined as the time after which, on gently tapping the grid, degraded polypropylene drops out in the form of a powder (checked 1 – 2 x daily). The results are quoted in hours.

Table 5

| Stabiliser No. | Hours to incipient decomposition | |
|---|---|---|
| | 147°C | 135°C |
| without additive | 10 | 20 |
| 1 | 190 | 1,220 |
| 2 | 160 | 1,145 |
| 3 | 120 | 410 |
| 4 | 150 | 420 |
| 5 | 160 | 450 |
| 6 | 165 | 580 |
| 7 | 120 | 420 |
| 8 | 130 | 380 |
| 9 | 170 | 450 |
| 10 | 160 | 480 |
| 11 | 170 | 510 |
| 12 | 160 | 330 |
| 13 | 155 | 520 |
| 14 | 170 | 720 |
| 15 | 150 | 550 |
| 16 | 150 | 490 |

EXAMPLE 20

1 gram portions of the filings (chips) described in Example 18 are stirred for 30 minutes in 100 ml of chloroform at room temperature and then filtered off and dried. Aging of the filings treated in this way, in a circulating air oven at 147°C, gives the results in Table 6. The end point is defined as the time after which, on gently tapping, degraded polypropylene drops out of the suspension grid. The results are quoted in hours.

Table 6

| Stabiliser No. | Hours to incipient decomposition at 147°C |
|---|---|
| without additive | 10 |
| 1 | 140 |
| 2 | 130 |
| 3 | 100 |
| 4 | 100 |
| 5 | 100 |
| 6 | 120 |
| 7 | 120 |
| 8 | 110 |
| 9 | 130 |
| 13 | 130 |

As can be seen from the results in Table 6, the good anti-oxidative protective action of the compounds according to the invention remains preserved even after extraction.

EXAMPLE 21

1 kg of polypropylene (melt index 1.3 g/10 minutes, 230°C/2,160 g) is thoroughly mixed for 10 minutes in a shaking apparatus with 1.0 g of one of the additives listed in Table 7 below.

The resulting mixture is extruded in a laboratory single-screw extruder ("Plamvo") at 260°C nozzle temperature/100 revolutions/minute, with a throughput of 50 g/minute, and is subsequently granulated. The melt index of the resulting granules can be seen in Table 7 below, column 2. The granules are subsequently regranulated 4 more times (extrusions 2–5) under the conditions indicated above, the melt indices being measured after the 3rd extrusion and again after the 5th extrusion. (Table below, columns 3 and 4). Whilst the unstabilised polypropylene shows a marked rise in the melt index and hence severe degradation, the stabilising action of the additives can be seen from the table:

Table 7

| Stabiliser No. | Melt index after 1st extrusion in g/10 minutes | Melt index after 3rd extrusion in g/10 minutes | Melt index after 5th extrusion in g/10 minutes |
|---|---|---|---|
| — | 5.6 | 17.5 | 45.0 |
| 1 | 2.1 | 3.4 | 4.5 |
| 3 | 2.3 | 4.6 | 6.4 |
| 5 | 2.4 | 4.9 | 7.0 |
| 6 | 3.1 | 5.8 | 7.4 |
| 10 | 3.2 | 3.6 | 5.8 |
| 14 | 2.3 | 4.5 | 5.0 |

EXAMPLE 22

100 parts of polyamide 6 granules are mixed with 0.5 part of tris-nonylphenylphosphite and 0.5 part of one of the additives listed in Table 8 below, processed in a laboratory Gelimat and thereafter pressed at 260°C to give 1 mm test sheets. The sheets are subjected to an accelerated aging in a circulating air oven at 140°C. The stabilising action of the additives is assessed from the brittleness of the sheets.

Table 8

| Stabiliser No. | Brittle after |
|---|---|
| — | 18 hours |
| 1 | 28 hours |
| 3 | 35 hours |
| 5 | 25 hours |
| 6 | 25 hours |
| 8 | 40 hours |

EXAMPLE 23

Commercial EPDM rubber from Dutch Staatsmijnen is freed of stabiliser by dissolving in hot toluene and precipitating with methanol. 40 g samples of the dried stabiliser-free material together with 0.2 % of one of the additives listed in Table 9 below are kneaded in a Brabender plastograph, whilst continuously recording the torque caused by the kneading resistance. (Table: torque directly read on the balance, in grams). At the same time, the gel content (hexane-insoluble constituents) was examined in one sample after 7.15 and one sample after 25 minutes. The gel contents increase with progressive aging, that is to say crosslinking of the polymer.

Table 9

| Stabiliser No. | Torque in grams after: | | |
|---|---|---|---|
| | 7 minutes | 15 minutes | 25 minutes |
| — | 3,900 | 3,200 | 2,500 |
| 1 | 3,800 | 3,500 | 3,500 |
| 3 | 3,700 | 3,200 | 3,200 |
| 9 | 3,600 | 3,400 | 3,400 |

| | Gel content in per cent after: | | |
|---|---|---|---|
| | 7 minutes | 15 minutes | 25 minutes |
| — | 3 | 20 | 35 |
| 1 | 0 | 4 | 8 |
| 3 | 0 | 1 | 8 |
| 9 | 0 | 2 | 10 |

EXAMPLE 24

100 parts of unstabilised homopolyacetal (polyformaldehyde, origin: Societa Italiana Resine) are mixed with 1.5 parts of calcium stearate and 0.2 part of one of the additives mentioned in Table 10 below, the mixture is processed for 15 minutes on a twin-rill mill and the mill hide is drawn off. 10 mg portions of the stabilised samples are heated to 220°C on the pan of a sensitive thermo-balance. The weight loss of the samples, which indicates the progressive aging, is recorded continuously.

Table 10

| Stabiliser No. | Weight loss in % after | | |
|---|---|---|---|
| | 5 minutes | 10 minutes | 15 minutes |
| — | 12 | 22 | 31 |
| 1 | 4 | 9 | 14 |
| 3 | 3 | 12 | 18 |
| 9 | 4 | 7 | 13 |

What we claim is:

1. A polymer resin of the general formula I

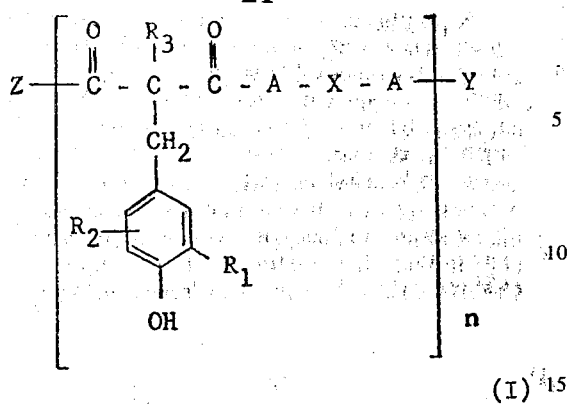

(I)

wherein $R_1$ and $R_2$ denote alkyl with 1 to 5 carbon atoms, cycloalkyl with 6 to 8 carbon atoms or aralkyl with 7 to 9 carbon atoms, $R_3$ denotes hydrogen, alkyl with 1 to 18 carbon atoms, or the group

A denotes —O—; —NH—; or $$-\underset{R_4}{\underset{|}{N}}-$$

wherein $R_4$ is an alkyl group with 1 – 4 carbon atoms, X denotes alkylene with 2 to 18 carbon atoms, alkenylene with 4 to 18 carbon atoms wherein A is directly linked to a saturated carbon atom in the alkenylene, oxaalkylene with 4 to 18 carbon atoms wherein A is directly linked to a carbon atom in the oxaalkylene which does not carry any further hetero-atoms, thiaalkylene with 4 to 18 carbon atoms wherein A is directly linked to a carbon atom in the thiaalkylene which does not carry any further hetero-atoms, mercaptoalkylene with 3 to 18 carbon atoms, alkylthioalkylene with 4 to 21 carbon atoms, hydroxyalkylene with 3 to 18 carbon atoms, acyloxyalkylene with 5 to 21 carbon atoms, phenoxyalkylene with 9 to 20 carbon atoms, or alkoxyalkylene with 4 to 21 carbon atoms, wherein the mercapto, alkylthio, hydroxyl, acyloxy, phenoxy or alkoxy group of the mercaptoalkylene, alkylthioalkylene, hydroxyalkylene, acyloxyalkylene, phenoxyalkylene or alkoxyalkylene is bonded to a carbon atom not linked to the group A, or a group

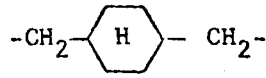

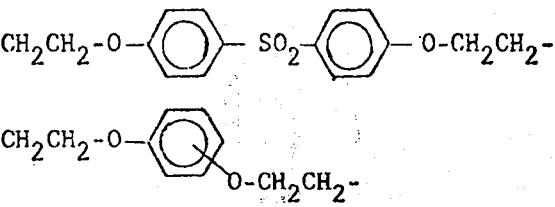

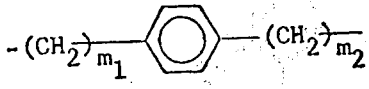

wherein $m_1$ and $m_2$ are 1, 2, or 3, Y denotes hydrogen or the group

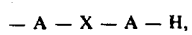

Z denotes $OR_5$ or, if Y denotes hydrogen, also denotes the group $$- A - X - A - H,$$

with the abovementioned meanings for A and X and $R_5$ denotes hydrogen, alkyl with 1 to 18 carbon atoms, oxaalkyl with 3 to 20 carbon atoms, wherein the carbon atom in $R_5$ linked to oxygen does not carry any further hetero-atoms, thiaalkyl with 3 to 20 carbon atoms wherein the carbon atom in $R_5$ linked to the oxygen does not carry any further hetero-atoms, or 1-phospha-2,6,7-trioxabicyclo[2,2,2]-oct-4-yl-methyl, and $n$ denotes 2 to 100.

2. A polymer resin according to claim 1, of the formula I, wherein $R_1$ denotes methyl, isopropyl, sec.-butyl or tert.-butyl, $R_2$ denotes hydrogen or methyl, isopropyl, sec.-butyl, or tert.-butyl, $R_3$ denotes hydrogen or the group

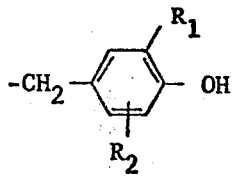

A denotes —O— or —NH—, X denotes alkylene with 2 to 18 carbon atoms or thiaalkylene with 4 to 18 carbon atoms, A being linked directly to a carbon atom in the thiaalkylene which does not carry any further hetero-atoms, Y denotes hydrogen or the group

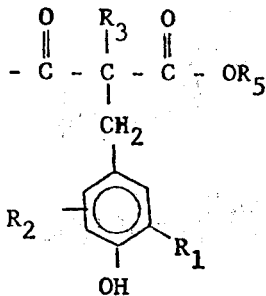

Z denotes $OR_5$ or, if Y denotes hydrogen, also denotes the group

— A — X — A — H, with the abovementioned meanings for A and X, $R_5$ denotes hydrogen, alkyl with 1 to 18 carbon atoms or thiaalkyl with 3 to 20 carbon atoms, wherein the carbon atom in $R_5$ bonded to oxygen does not carry any further hetero-atoms and n denotes 2 to 50.

3. A polymer resin according to claim 1, of the formula I, wherein $R_1$ denotes alkyl with 1 to 4 carbon atoms, $R_2$ denotes alkyl with 4 carbon atoms, $R_3$ denotes hydrogen, A denotes —O— or —NH—, X denotes alkylene with 5 to 9 carbon atoms, thiaalkylene with 4 carbon atoms, alkylthioalkylene with 21 carbon atoms, alkoxyalkylene with 21 carbon atoms, wherein A is linked to a carbon atom in the thiaalkylene, alkylthioalkylene or alkoxyalkylene which does not carry any further hetero-atoms, or the group —$CH_2$-CHOH—$CH_2$—, Y denotes hydrogen or the group

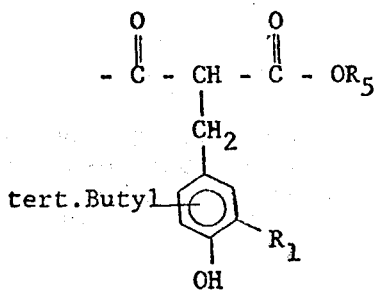

with $R_1$ being alkyl with 1 to 4 carbon atoms, and $R_5$ being alkyl with 1 to 18 carbon atoms, Z denotes alkoxy with 1 to 18 carbon atoms or 1-phospha-2,6,7-trioxabicyclo[2,2,2]oct-4-yl-methyl and n denotes 2 – 20.

* * * * *